United States Patent
Li et al.

(10) Patent No.: US 6,503,228 B1
(45) Date of Patent: Jan. 7, 2003

(54) PROTECTIVE ASSEMBLY FOR A PERCUTANEOUS ACCESS DEVICE

(75) Inventors: Jun Li, Westland, MI (US); Adrian Kantrowitz, Auburn Hills, MI (US); Paul Freed, Bloomfield Hills, MI (US); George Taro, Canton, MI (US)

(73) Assignee: L-Vad Technology, Inc., Detroit, MI (US)

(*) Notice: Subject to any disclaimer, the term of this patent is extended or adjusted under 35 U.S.C. 154(b) by 0 days.

(21) Appl. No.: 09/539,938

(22) Filed: Mar. 31, 2000

(51) Int. Cl.⁷ .............................................. A61M 5/32
(52) U.S. Cl. ...................................... 604/175; 604/197
(58) Field of Search ......................... 604/500, 502, 604/93.01, 288.01–288.04, 164.04, 164.07, 164.08, 197, 264, 175, 891.1

(56) References Cited

U.S. PATENT DOCUMENTS

| | | | |
|---|---|---|---|
| 3,694,819 A | 10/1972 | Meyer | 3/1 |
| 3,765,032 A | 10/1973 | Palma | 3/1 |
| 3,783,868 A | 1/1974 | Bokros | 128/260 |
| 4,025,964 A | 5/1977 | Owens | 3/1 |
| 4,321,914 A | 3/1982 | Begovac et al. | 128/1 R |
| 4,344,435 A | 8/1982 | Aubin | 128/350 R |
| 4,496,349 A | 1/1985 | Cosentino | 604/175 |
| 4,534,761 A | 8/1985 | Raible | 604/175 |
| 4,662,890 A | 5/1987 | Burton | 623/66 |
| 4,676,802 A | 6/1987 | Tofield et al. | 623/66 |
| 4,753,656 A | 6/1988 | Tofield et al. | 623/15 |
| 5,176,662 A * | 1/1993 | Bartholomew et al. | 128/DIG. 26 |
| 5,205,286 A | 4/1993 | Soukup et al. | 128/630 |
| 5,300,086 A | 4/1994 | Gory et al. | 606/200 |
| 5,423,334 A | 6/1995 | Jordan | 128/899 |
| 5,507,303 A | 4/1996 | Kuzma | 128/899 |
| 5,741,298 A | 4/1998 | MacLeod | 606/213 |
| 5,868,699 A * | 2/1999 | Woodruff et al. | 604/60 |
| 5,873,368 A | 2/1999 | Sabin | 128/899 |
| 5,895,351 A * | 4/1999 | Nottage et al. | 600/201 |
| 5,968,011 A * | 10/1999 | Larsen et al. | 604/93 |

* cited by examiner

*Primary Examiner*—Anhtuan T. Nguyen
*Assistant Examiner*—Kevin C. Sirmons
(74) *Attorney, Agent, or Firm*—Gifford, Krass, Groh, Sprinkle, Anderson & Citkowski, P.C.

(57) ABSTRACT

A protective assembly for a protruding portal shields a neck portion of the portal. The protective assembly is well suited for shielding a percutaneous access device during surgical implantation. The protective assembly includes a lid seating pin configured to seat within the interior of the portal and a lid secured to the pin extending over exterior portions of the portal and gapped from the portal face and the neck. Optionally, the pin inserts within a temporary turret engaging the interior of the portal.

22 Claims, 3 Drawing Sheets

PROTECTIVE ASSEMBLY FOR A PERCUTANEOUS ACCESS DEVICE

FIELD OF THE INVENTION

The present invention relates to a protective assembly to protect the access portal from adverse contact during surgical implantation of the device.

BACKGROUND OF THE INVENTION

An increasing number of medical procedures involve the permanent implantation of electrical and mechanical devices within an individual's body. The conveyance of power and electrical signals between implanted devices and external items of equipment necessitates the implantation of a coupler within an individual's skin. A percutaneous access device (PAD) is a typical conduit for the conveyance of electrical signals and pneumatic drive power between implanted mechanical devices and exterior equipment. Implanted devices in communication with external equipment by way of a PAD illustratively includes mechanical auxiliary ventricle (MAV), chronic ambulatory peritoneal dialysis, and cochlear stimulators.

To facilitate stability of the PAD structure within the skin, autologous cells of an individual are grown on neck surfaces of the PAD which are adjacent to an individual's epidermis following implantation. During a first surgical procedure, a skin incision is made by a trephine in order to correctly position and orient the PAD. During the course of implant surgery, the PAD is in contact with the incision edges as it is translated within the incision to attain proper orientation. In the course of contacting the incision edges, the autologous cells grown on the neck surfaces of the PAD are readily abraded and dislodged from the neck surfaces. As a result, current surgical procedures associated with PAD implantation do not fully realize the advantages associated with autologous cell culturing on the PAD neck surfaces prior to implantation.

Immediately following PAD implantation, a temporary plug is utilized to seal the PAD portal while granulation and cell growth occurs about the PAD neck surfaces to firmly secure the PAD within the skin. Typically, a temporary plug is required for about two to three weeks to keep the inner surfaces of the PAD free of contamination. Currently, a rubber stopper is utilized as a temporary plug. The rubber stopper is limited in its utility by having only a pressure fit along a limited contact surface to maintain the rubber stopper within the PAD portal. Thus, there exists a potential for the rubber stopper to become dislodged thereby exposing the inner PAD surfaces to contaminating effects of body fluid or air borne microbes. Thus, there remains a need for a protective assembly to protect the cell cultured surface during implantation and to temporarily shield a percutaneous access device from the environment without compromising the physical or biological barrier between the inner surfaces of a PAD.

SUMMARY OF THE INVENTION

A protective assembly for a protruding portal having an interior, a face, and a neck is described including a protective lid having a surface gapped from the portal face and neck and a lid seating pin extending into the interior of the portal and engaging the protective lid surface. The protective assembly is particularly well suited for protecting a percutaneous access device portal.

A protective assembly for a percutaneous access device includes a turret adapted to seat within the device, the turret having a base, an exterior wall and an inner wall terminating at an upper edge to form a cup, the turret base having a through hole therein. A screw selectively secures the turret to the percutaneous access device. A lid centering pin is adapted to fit within the cup, the pin having lateral dimensions such that the sidewalls are adjacent the inner wall of the turret upon fitting the pin into the cup, the top surface having at least one blind hole therein. A protective lid having a lip extending from a cover surface, the covering surface having an aperture aligned with at least one blind hole and the lid centering pin such that the lip surrounding the outer surface of the percutaneous access device forms a gap therewith. At least one screw engages at least one blind hole and the aperture to selectively secure the lid to the portal such that the cover surface contacts the upper edge of the turret or the top surface of the lid centering pin.

A method of protecting a percutaneous access device having an interior, a face, and a neck includes the steps of removably inserting a lid seating pin into the interior of the percutaneous access device and securing a protective lid to the lid seating pin so that the lid is gapped from the face and the neck of the percutaneous access device. A commercial package includes a lid seating pin adapted to fit within the interior of the percutaneous access device as well as a protective lid secured to the pin which forms a gapped cover over an exposed face and exterior of the percutaneous access device along with instructions for the use thereof as a temporary covering.

BRIEF DESCRIPTION OF THE DRAWINGS

The present invention is described in greater detail by reference to the accompanying drawings which are exemplary and not intended as limitations on the scope of the invention wherein.

PREFERRED EMBODIMENT OF THE INVENTION

The present invention finds utility as a protective assembly for a protruding portal which is adapted to form a removable barrier. A portal is secured in a predetermined location. The portal characterized by having an interior surface in electrical and/or fluid communication with the rearward portion of the portal. The portal inner surface being defined by sidewalls terminating in a face. The face typically being formed to a high degree of tolerance necessary for coupling of a fitting thereto. While the present invention is described in the context of a percutaneous access device, it is appreciated that a protective assembly according to the present invention has utility in the context of portals adapted for applications illustratively including compressed gas, biological fluids, and in extreme thermal or corrosive environments such as marine settings.

Figure 1:
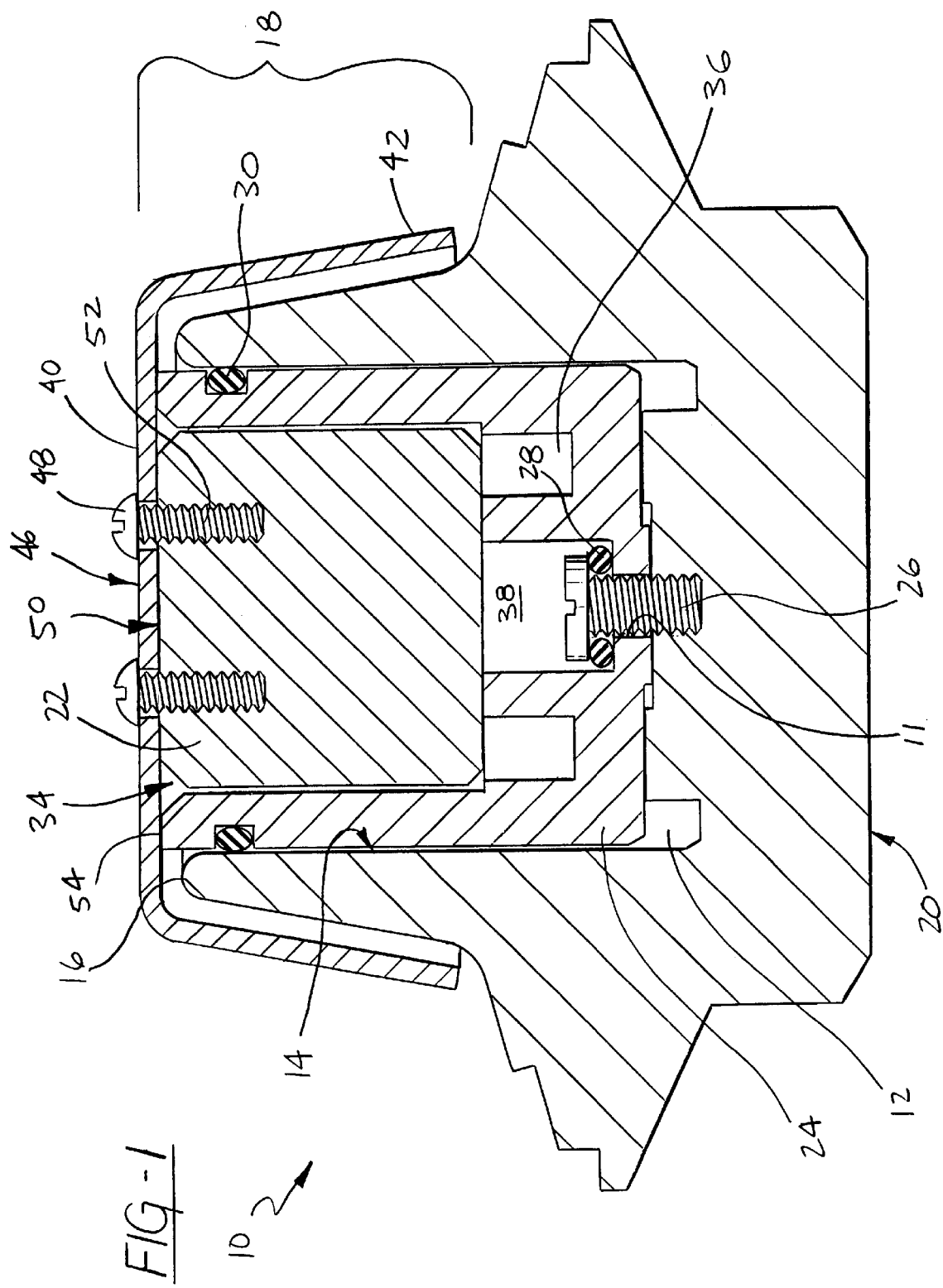
FIG. 1 is a cross sectional view of an embodiment of the present invention through a region of epidermis having an embodiment of a PAD and a protective assembly according to the present invention applied thereto.
Figure 2:
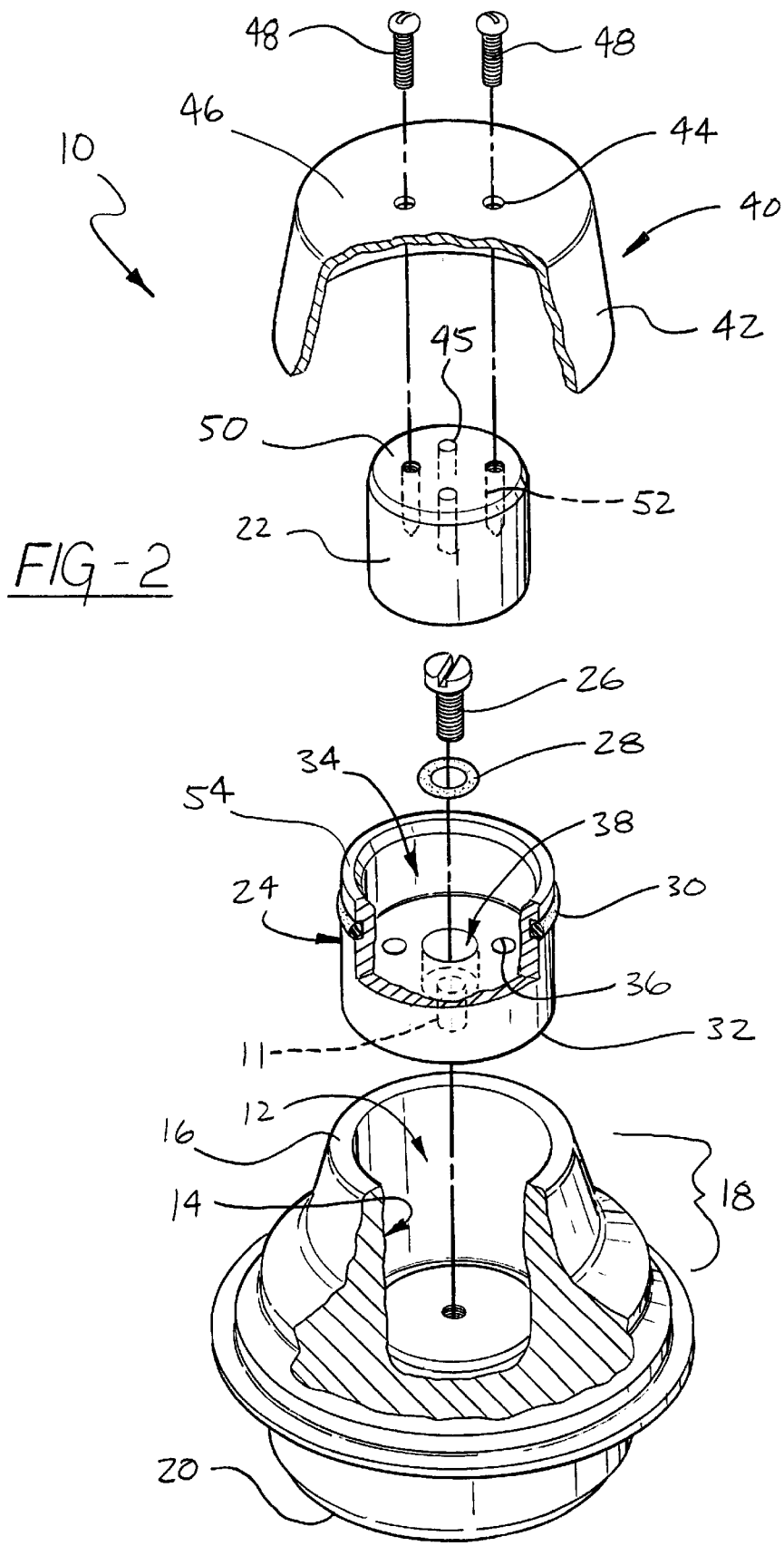
FIG. 2 is an exploded partial cutaway perspective view of the protective assembly embodiment shown in FIG. 1.

Referring now to FIGS. 1 and 2, a portal 10 is shown having an interior 12. The interior 12 being defined by a sidewall 14 terminating in a portal face 16. The portal 10 depicted is operative as a percutaneous access device and further includes a neck region 18 adapted to promote growth of autologous fibroblast cells thereon. At least one fluid or electrical contact is made to the rearward portal face 20 by way of the portal interior 12 (not shown). The fluid being in a gaseous or liquid phase.

A lid seating pin 22 is formed to seat within the interior 12 of the portal 10. While a lid seating pin 22 according to the present invention is optionally formed to securely seat within the interior 12 of the portal 10, preferably, a lid seating pin 22 seats within a temporary turret 24 that simultaneously engages the interior 12 and the lid seating pin 22. More preferably, the temporary turret 24 is held within the interior 12 by a screw 26 urging the temporary turret 24 into secure contact with the interior 12 by engaging a complementary thread hole 11 of the portal 10. Most preferably, airtight O-ring seals 28 and 30 isolate sensitive surfaces of the interior 12 from the exterior environment adjacent to the portal face 16, respectively. An O-ring in the present invention is formed of conventional materials illustratively including neoprene. A temporary turret according to the present invention functions as a concentric rack for the protective lid centering pin complex during insertion and removal as well as isolating sensitive surfaces of the PAD interior prior to PAD coupling to exterior medical devices. A temporary turret 24 includes a cup 34 therein adapted to receive a lid seating pin. Preferably, the interior 12, temporary turret 24 and lid seating pin 22 are concentric. More preferably, the interior 12, temporary turret 24 and lid seating pin 22 are generally right cylindrical features. A temporary turret 24 of the present invention optionally includes at least one blind hole 36 extending beneath the turret cup 34. Preferably, where a blind hole 36 is spaced from the central axis of the temporary turret 24, at least one additional blind hole is spaced from the blind hole 36 in order to balance the forces applied thereto in the course of installation or removal of a temporary turret from the interior 12 of the portal 10. The blind hole 36 is optionally present as an insertion point for a surgical instrument illustratively including a Kelly hemostat for the installation or removal of the temporary turret. Alternatively, the temporary turret 24 is removed through selectively securing a matched threaded bolt (not shown) to the threaded hole 38. Preferably, the threaded hole 38 is centered within the temporary turret 24 to promote equilateral forces on the temporary turret and portal 10 during removal or installation of the turret 24.

A turret and pin according to the present invention being formed of a variety of materials chosen based upon factors including strength, durability, sterilizability and manufacturability. Operative materials include stainless steel, Teflon, Delrin, or other engineered plastics. It is appreciated that a plastic turret or pin is readily adapted to receive insert sleeves of a harder material such as brass or steel to serve as contact surfaces for fasteners, forceps and other disengageable components.

In those embodiments of the present invention wherein a lid seating pin is fit directly to the interior 12, the height of the lid seating pin 22 is such that upon resting securely within the interior 12, the exposed pin surface extends beyond the portal face 16.

The lid seating pin 22 is adapted to selectively secure a protective lid generally shown at 40. A protective lid of the present invention functions to protect cells growing on the PAD neck region 18. In order to avoid abrasion of cultured cell layers on the PAD neck, it is preferred that the protective lid 40 is gapped away from the portal face 16 and the neck region 18 so as to prevent contact therewith yet leave a minimal gap to lessen stretching of the skin. Typically, the gap between a protective lid and portal surfaces is between 0.1 and 0.75 millimeters. Ideally the gap is between 0.2 and 0.4 millimeters. More preferably, the extending lip 42 of the protective lid 40 complements the contours of the portal neck region 18. In the embodiment of the present invention depicted in FIGS. 1 and 2, extending lip 42 tapers at an angle of 9 degrees relative to the central axis of the portal 10. The angle of the extending lip 42 approximately parallels the contours of the neck region 18. A protective lid of the present invention can be constructed from a variety of materials including stainless steel, plastic, titanium and laminates thereof. Preferably, protective lid 40 is constructed of stainless steel. The protective lid 40 contains at least one aperture 44 extending through a cover surface 46 for securing the protective lid 40 to the lid seating pin 22 by way of a fastener 48. While the protective lid is depicted in the accompanying figures as being secured to the lid seating pin 22 by way of a fastener 48 engaging complementary threads within the lid seating pin 22, it is appreciated that other fastening systems exist for securing a protective lid in a position relative to seating pin 22. For instance, a unitary component having an extending lip and an integral pin adapted to securely seat within the interior of a portal is readily constructed. Alternatively, complementary lock and key portions of a protective lid and seating pin are added (not shown). Further, while the top surface 50 of the lid seating pin 22 and the complementary surface 46 of the protective lid 40 are depicted as being planar, it is appreciated that a nonplanar protective lid surface and/or lid seating pin extending face are operative herein.

The lid seating pin 22 serves to anchor protective lid 40. Optionally, an additional at least one blind bore 45 is formed in the top surface 50 of the lid seating pin 22. The lid seating pin 22 has at least one threaded hole 52 adapted to receive the fastener 48 and thereby secure the protective lid 40 to the lid seating pin 22. A blind bore in the lid seating pin 22 is utilized in the present invention to provide a contact point for a surgical instrument such as a Kelly hemostat, the surgical instrument being used in the process of installing or removing the protective assembly of the present invention. Optionally, a polymeric bushing (not shown) or film is inserted in the interface between turret cup 34 and lid seating pin 22 to facilitate smooth insertion and withdrawal. Preferably, the polymeric material is a perfluoropolyethylene material of a thickness suitable to cause a small but constant friction of the lid seating pin 22 relative to the cup 34.

The relative height of the temporary turret 24 and/or the top surface 50 of the lid seating pin 22 are selected according to the present invention to insure a contact surface for the protective lid 40 which is gapped relative to the portal face 16 and neck 18. Such a gap is created by extending either the cup 34 of temporary turret 24 above the portal face 16, extending face 50 of the lid seating pin 22 above the portal face 16, or extending both cup 34 and top surface 50 above the portal face 16. Preferably, both the cup 34 and the top surface 50 are extended above the portal face 16. More preferably, top surface 50 and cup edge 54 are flush. Most preferably, the top surface 50 and the cup edge 54 extend above the portal face 16 a distance approximately equal to the gap between the extending lip 42 and the neck region 18.

Figure 3A:
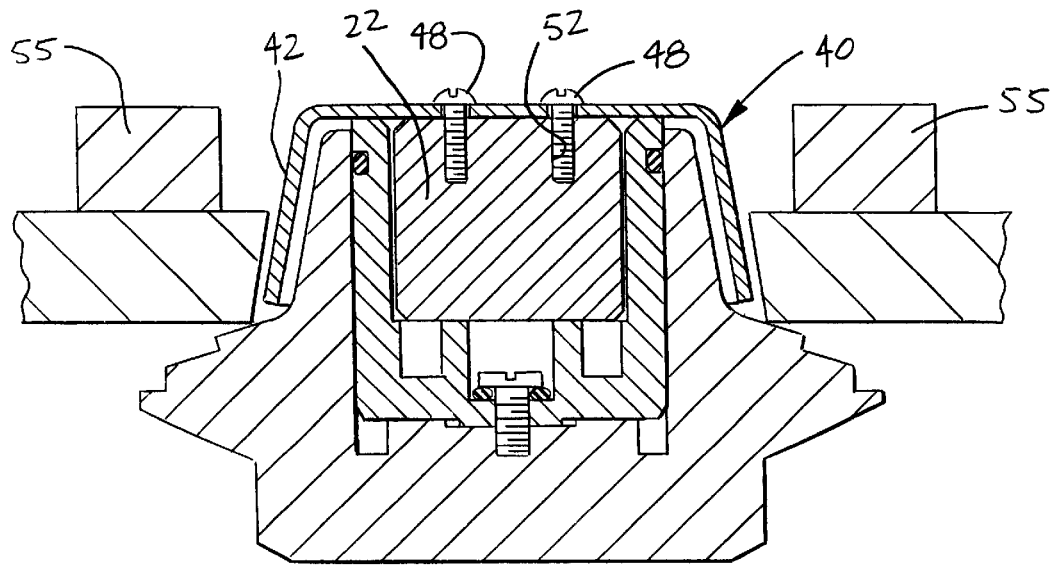
FIGS. 3A and B are cross sectional views of events associated with the deployment of the present invention.
Figure 3B:
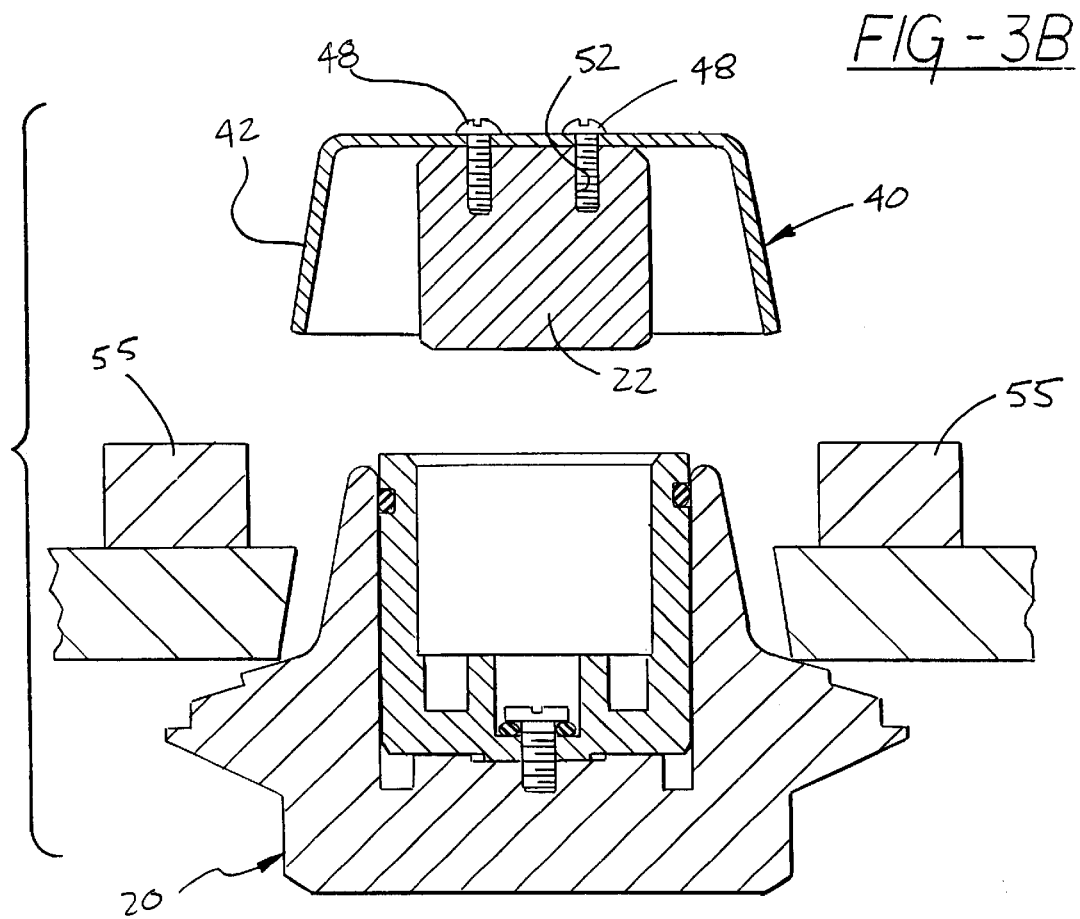

As shown in FIGS. 3A and 3B, an auxiliary ring 55 is used to provide a counter force against the skin during removal of the protective lid when the protected PAD is in place. The auxiliary ring has an inner diameter larger than the outer diameter of the protective lid. Preferably, the auxiliary ring 55 is constructed of perfluoropolyethylene.

The foregoing description is illustrative of particular embodiments of the invention, but is not meant to be a limitation upon the practice thereof. The following claims, including all equivalents thereof, are intended to define the scope of the invention.

What is claimed is:

1. A protective assembly for a portal, said assembly comprising:

a protruding portal having an interior, a face and a neck;

a protective lid having a surface gapped from the face and the neck;

a lid seating pin extending into the interior of said protruding portal and engaging said lid; and a turret forming essentially a right cylinder adapted to seat within the interior of said portal, said turret having a base and inner wall terminating at an upper edge so as to form a cup, wherein said pin engages the cup.

2. A protective assembly for a portal, said assembly comprising:

a protruding portal having an interior, a face and a neck;

a protective lid having a surface gapped from the face and the neck;

a lid seating pin extending into the interior of said protruding portal and engaging said lid;

a turret adapted to seat within the interior of said portal, said turret having a base and inner wall terminating at an upper edge so as to form a cup, wherein said pin engages the cup; and a screw selectively securing said turret to said portal.

3. A protective assembly for a portal, said assembly comprising:

a protruding portal having an interior, a face and a neck;

a protective lid having a surface gapped from the face and the neck;

a lid seating pin extending into the interior of said protruding portal and engaging said lid; and a turret adapted to seat within the interior of said portal, said turret having a base and inner wall terminating at an upper edge so as to form a cup, wherein said pin engages the cup and the upper edge of said turret contacts the portal facing surface of said protective lid.

4. A protective assembly for a percutaneous access device comprising:

a turret adapted to seat within said device, said turret having a base, an exterior wall and an inner wall terminating at an upper edge so as to form a cup, the base having a through hole;

a screw selectively securing said turret to said device;

a lid centering pin adapted to fit within the cup, said pin having side walls and a top surface, said pin having lateral dimensions such that the side walls are adjacent to the inner wall upon fitting said pin into the cup, the top surface having at least one blind hole therein;

a protective lid having a lip extending from a cover surface, the cover surface having an aperture aligning with the at least one hole upon said lid engaging said pin, the lip surrounding the outer surface of the protruding part of said device and forming a gap therewith; and at least one screw adapted to engage the at least one blind hole and the aperture to selectively secure said lid to said pin such that the cover surface contacts the upper edge of said turret.

5. The assembly of claim 4 wherein the base of said turret has at least two blind base holes.

6. The assembly of claim 4 wherein said screw is selectively engaged to urge said turret against said portal.

7. The assembly of claim 4 further comprising a first O-ring placed about said screw and in contact with the base of said turret upon selectively securing said turret to said device.

8. The assembly of claim 7 further comprising a second O-ring simultaneously in contact with the exterior of said turret and said device.

9. The assembly of claim 8 wherein said first and second O-rings form a fluid barrier within said device.

10. The assembly of claims 4 wherein the cup of said turret forms essentially a right cylinder.

11. The assembly of claim 4 wherein the inner wall of said turret has a tapered edge at the upper edge.

12. The assembly of claim 4 wherein said pin forms essentially a right cylinder.

13. The assembly of claim 4 wherein the cup and said pin are concentric.

14. The assembly of claim 4 further comprising a plurality of blind holes in the top surface of said pin and a plurality of apertures in said lid such that each of said plurality of holes aligns with one of said plurality of apertures upon said lid engaging said pin, providing handles for pushing in and pulling off the lid-pin assembly from the cup of said turret.

15. The assembly of claim 4 wherein said pin is tapered at its bottom edge to promote the engagement with the cup of said turret.

16. The assembly of claim 4 wherein said protective lid is constructed of a material comprising stainless steel.

17. The assembly of claim 4 wherein the cover of said lid contacts the upper edge of said turret upon engagement.

18. The assembly of claim 4 further comprising an auxiliary ring to provide a counter force against the skin during removal of said protective assembly.

19. The assembly of claim 18 wherein said ring has an inner diameter larger than the outer diameter of said lid.

20. The assembly of claim 18 wherein said ring comprises perfluoropolyethylene.

21. The assembly of claim 4 further comprising a deformable film ring bounded by the inner wall of said turret and the side walls of said pin.

22. The assembly of claim 21 wherein said deformable film ring comprises a polymeric material.

* * * * *